US012329971B2

(12) United States Patent
Parker et al.

(10) Patent No.: US 12,329,971 B2
(45) Date of Patent: Jun. 17, 2025

(54) ADAPTATION OF NEUROSTIMULATION THERAPY TO AGE-RELATED PHYSIOLOGICAL CHANGES

(71) Applicant: Saluda Medical Pty Ltd, Artarmon (AU)

(72) Inventors: John Louis Parker, Artarmon (AU); Peter Scott Vallack Single, Artarmon (AU); Dean Michael Karantonis, Artarmon (AU); Matthew Marlon Williams, Artarmon (AU); Daniel John Parker, Artarmon (AU); Samuel Nicholas Gilbert, Artarmon (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 340 days.

(21) Appl. No.: 17/812,959

(22) Filed: Jul. 15, 2022

(65) Prior Publication Data
US 2023/0014405 A1 Jan. 19, 2023

(30) Foreign Application Priority Data
Jul. 16, 2021 (AU) .................. 2021902202

(51) Int. Cl.
*A61N 1/36* (2006.01)
(52) U.S. Cl.
CPC .................. *A61N 1/36139* (2013.01)
(58) Field of Classification Search
None
See application file for complete search history.

(56) References Cited

U.S. PATENT DOCUMENTS

| | | | |
|---|---|---|---|
| 7,801,618 B2 | 9/2010 | Pless | |
| 8,838,241 B1 | 9/2014 | Ness et al. | |
| 9,119,965 B2 | 9/2015 | Xi et al. | |
| 9,421,379 B2 | 8/2016 | Zhu | |
| 9,529,972 B2 | 12/2016 | Giftakis et al. | |
| 10,265,518 B2 | 4/2019 | Yu | |
| 10,729,905 B2 | 8/2020 | Annoni et al. | |
| 11,198,001 B1 | 12/2021 | Thacker et al. | |
| 11,395,625 B2 | 7/2022 | Clark et al. | |
| 11,691,014 B2 | 7/2023 | Srivastava et al. | |
| 2008/0319511 A1* | 12/2008 | Pless | A61B 5/369 607/59 |
| 2010/0143256 A1* | 6/2010 | Suffin | A61B 5/411 424/9.2 |

(Continued)

FOREIGN PATENT DOCUMENTS

WO WO2009134478 A1 11/2009
WO WO2009137119 A1 11/2009

(Continued)

*Primary Examiner* — Ankit D Tejani
(74) *Attorney, Agent, or Firm* — Barnes & Thornburg LLP

(57) ABSTRACT

Disclosed is a method of adapting the operation of an implantable device for delivering neurostimulation therapy to a patient. The method comprises: delivering the neurostimulation therapy to electrically excitable tissue of the patient according to at least one therapy parameter; measuring a physiological characteristic of the patient; adjusting the at least one therapy parameter according to a schedule of adjustment and the measured physiological characteristic; and repeating the delivering, measuring, and adjusting.

21 Claims, 11 Drawing Sheets

(56) References Cited

U.S. PATENT DOCUMENTS

| | | |
|---|---|---|
| 2022/0387803 A1 | 12/2022 | Zenisek et al. |
| 2023/0338737 A1 | 10/2023 | Lee |

FOREIGN PATENT DOCUMENTS

| | | |
|---|---|---|
| WO | WO2012155183 A1 | 11/2012 |
| WO | WO2012155184 A1 | 11/2012 |
| WO | WO2012155188 A1 | 11/2012 |
| WO | WO2014197596 A1 | 12/2014 |
| WO | WO2015074121 A1 | 5/2015 |
| WO | WO2017123613 A1 | 7/2017 |
| WO | WO2017127902 A1 | 8/2017 |
| WO | WO2018034940 A1 | 2/2018 |
| WO | WO2018053336 A1 | 3/2018 |
| WO | WO2018063637 A1 | 4/2018 |
| WO | WO2018063912 A1 | 4/2018 |
| WO | WO2018080887 A1 | 5/2018 |
| WO | WO2018132529 A1 | 7/2018 |
| WO | WO2018132535 A1 | 7/2018 |
| WO | WO2019217071 A1 | 11/2019 |
| WO | WO2019217079 A1 | 11/2019 |
| WO | WO2021030152 A1 | 2/2021 |
| WO | WO2021080727 A1 | 4/2021 |
| WO | WO2021252257 A1 | 12/2021 |
| WO | WO2021252259 A1 | 12/2021 |
| WO | WO2022040757 A1 | 3/2022 |
| WO | WO2022177747 A1 | 8/2022 |
| WO | WO2022183194 A1 | 9/2022 |
| WO | WO2022183198 A1 | 9/2022 |
| WO | WO2022240580 A1 | 11/2022 |
| WO | WO2022251787 A1 | 12/2022 |
| WO | WO2022261001 A1 | 12/2022 |

\* cited by examiner

ADAPTATION OF NEUROSTIMULATION THERAPY TO AGE-RELATED PHYSIOLOGICAL CHANGES

RELATED APPLICATIONS

This application claims the benefit of Australian Provisional Patent Application No. 2021902202, filed 16 Jul. 2021 and incorporates by reference the entire disclosure thereof.

FIELD OF THE INVENTION

The present invention relates to neurostimulation therapy and in particular relates to methods of adapting such therapy to physiological changes related to the age of the patient.

BACKGROUND OF THE INVENTION

There are a range of situations in which it is desirable to apply neural stimuli in order to alter neural function, a process known as neuromodulation. For example, neuromodulation is used to treat a variety of disorders including chronic neuropathic pain, Parkinson's disease, and migraine. A neuromodulation system applies an electrical pulse (stimulus) to neural tissue (fibres, or neurons) in order to generate a therapeutic effect. In general, the electrical stimulus generated by a neuromodulation system evokes a response known as a neural action potential in a neural fibre which then has either an inhibitory or excitatory effect. Inhibitor effects can be used to modulate an undesired process such as the transmission of pain, or excitatory effects may be used to cause a desired effect such as the contraction of a muscle.

When used to relieve neuropathic pain originating in the trunk and limbs, the electrical pulse is applied to the dorsal column (DC) of the spinal cord, a procedure referred to as spinal cord stimulation (SCS). Such a system typically comprises an implanted electrical pulse generator, and a power source such as a battery that may be transcutaneously rechargeable by wireless means, such as inductive transfer. An electrode array is connected to the pulse generator, and is implanted adjacent the target neural fibre(s) in the spinal cord, typically in the dorsal epidural space above the dorsal column. An electrical pulse of sufficient intensity applied to the target neural fibres by a stimulus electrode causes the depolarisation of neurons in the fibres, which in turn generates a response known as an action potential in the fibres. Action potentials propagate along the fibres in orthodromic (in afferent fibres this means towards the head, or rostral) and antidromic (in afferent fibres this means towards the cauda, or caudal) directions. The fibres being stimulated in this way inhibit the transmission of pain from a region of the body innervated by the target neural fibres (the dermatome) to the brain. To sustain the pain relief effects, stimuli are applied repeatedly, for example at a frequency in the range of 30 Hz-100 Hz.

For effective and comfortable neuromodulation, it is necessary to maintain stimulus intensity above a recruitment threshold. Stimuli below the recruitment threshold will fail to recruit sufficient neurons to generate action potentials with a therapeutic effect. In almost all neuromodulation applications, response from a single class of fibre is desired, but the stimulus waveforms employed can evoke action potentials in other classes of fibres which cause unwanted side effects. In pain relief, it is therefore desirable to apply stimuli with intensity below a discomfort threshold, above which uncomfortable or painful percepts arise due to over-recruitment of $A\beta$ fibres. When recruitment is too large, $A\beta$ fibres produce uncomfortable sensations. Stimulation at high intensity may even recruit $A\beta$ fibres, which are sensory nerve fibres associated with acute pain, cold and pressure sensation. It is therefore desirable to maintain stimulus intensity within a therapeutic range between the recruitment threshold and the discomfort threshold.

The task of maintaining appropriate neural recruitment is made more difficult by electrode migration (change in position over time) and/or postural changes of the implant recipient (patient), either of which can significantly alter the neural recruitment arising from a given stimulus, and therefore the therapeutic range. There is room in the epidural space for the electrode array to move, and such array movement from migration or posture change alters the electrode-to-fibre distance and thus the recruitment efficacy of a given stimulus. Moreover, the spinal cord itself can move within the cerebrospinal fluid (CSF) with respect to the dura. During postural changes, the amount of CSF and/or the distance between the spinal cord and the electrode can change significantly. This effect is so large that postural changes alone can cause a previously comfortable and effective stimulus regime to become either ineffectual or painful.

Another control problem facing neuromodulation systems of all types is achieving neural recruitment at a sufficient level for therapeutic effect, but at minimal expenditure of energy. The power consumption of the stimulation paradigm has a direct effect on battery requirements which in turn affects the device's physical size and lifetime. For rechargeable systems, increased power consumption results in more frequent charging and, given that batteries only permit a limited number of charging cycles, ultimately this reduces the implanted lifetime of the device.

Attempts have been made to address such problems by way of feedback or closed-loop control, such as using the methods set forth in International Patent Publication No. WO2012/155188 by the present applicant, the contents of which are incorporated herein by reference. Feedback control seeks to compensate for relative nerve/electrode movement by controlling the intensity of the delivered stimuli so as to maintain a substantially constant neural recruitment. The intensity of a neural response evoked by a stimulus may be used as a feedback variable representative of the amount of neural recruitment. A signal representative of the neural response may be sensed by a measurement electrode in electrical communication with the recruited neural fibres, and processed to obtain the feedback variable. Based on the response intensity, the intensity of the applied stimulus may be adjusted to maintain the response intensity within a therapeutic range.

It is therefore desirable to accurately detect and record a neural response evoked by the stimulus. The action potentials generated by the depolarisation of a large number of fibres by a stimulus sum to form a measurable signal known as an evoked compound action potential (ECAP). Accordingly, an ECAP is the sum of responses from a large number of single fibre action potentials. The ECAP generated from the depolarisation of a group of similar fibres may be measured at a measurement electrode as a positive peak potential, then a negative peak, followed by a second positive peak. This morphology is caused by the region of activation passing the measurement electrode as the action potentials propagate along the individual fibres.

Approaches proposed for obtaining a neural response measurement are described by the present applicant in International Patent Publication No. WO2012/155183, the content of which is incorporated herein by reference.

As the human body ages, certain physiological characteristics that play a role in neurostimulation therapy, such as SCS for chronic pain management, start to change in a way that reduces the efficacy of the therapy. This either results in more frequent visits by the patient to a clinic for reprogramming the implantable pulse generator, which is costly, inconvenient, and time-consuming, or a worsening of the patient's symptoms.

Therefore, a need exists for an implantable pulse generator that can autonomously adapt to the deterioration of neurostimulation-related characteristics with age.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood to mean that the element may be any one of the listed options, or may be any combination of two or more of the listed options.

SUMMARY OF THE INVENTION

Disclosed herein are implantable devices capable of, and methods for, self-reprogramming to adapt the therapy to age-related effects. The disclosed methods and devices are configured to adapt the therapy parameters (e.g. stimulus intensity for open-loop, or ECAP target, charge delivered per pulse, stimulation frequency, ECAP detector parameters, and/or feedback loop parameters for closed-loop) gradually over time to compensate for the age-related effects, according to a schedule of adjustment. The schedule of adjustments may itself be altered in response to measurements of age-related physiological characteristics that are relevant to neurostimulation.

According to a first aspect of the present technology, there is provided a method of adapting the operation of an implantable device for delivering neurostimulation therapy to a patient. The method comprises: delivering the neurostimulation therapy to electrically excitable tissue of the patient according to at least one therapy parameter; measuring a physiological characteristic of the patient; adjusting the at least one therapy parameter according to a schedule of adjustment and the measured physiological characteristic; and repeating the delivering, measuring, and adjusting.

According to a second aspect of the present technology, there is provided an implantable device for delivering neurostimulation therapy to a patient. The device comprises: an electrode array comprising a plurality of electrodes; a pulse generator connectable to the electrode array, the pulse generator configured to generate a stimulus pulse via the stimulus electrodes to electrically excitable tissue of the patient; and a controller. The controller is configured to: control the pulse generator to generate the stimulus pulse according to at least one therapy parameter; measure a physiological characteristic of the patient; adjust the at least one therapy parameter according to a schedule of adjustment and the measured physiological characteristic; and repeat the generate, measure, and adjust.

The schedule of adjustment may be a predefined schedule stored in the device, such as a lookup table or a linear or exponential ramp.

In some embodiments the measured physiological characteristic may comprise one or more of:
the patient's ECAP threshold measured in a reference posture, for example in mA;
the patient's sensitivity in a reference posture, for example the slope of a linear portion of the growth curve measured in $\mu V/mA$;
the patient's ECAP conduction velocity, for example as measured by latency from stimulus to measurement, and/or by latency between two spaced apart measurement sites;
the patient's ECAP dispersion, for example as measured by an ECAP peak width at a reference recruitment level, such as ECAP half-height peak width;
the patient's maximum tolerable stimulus intensity in a reference posture;
the patient's therapeutic window in a reference posture;
the patient's ECAP latency;
the patient's activation plot variation with posture, corresponding to patient mobility and flexibility;
the patient's daily activity;
a reaction time of the patient;
a measurement of grip strength of the patient;
a measurement of maximum heart rate or heart rate variation of the patient during activity; and
a measurement of forced expiratory volume of the patient.

In some embodiments the neurostimulation therapy is delivered in an open loop manner. In such embodiments the schedule of adjustment may provide for the at least one therapy parameter to be adjusted in a gradual manner corresponding to patient aging, such as monotonically. In such embodiments the schedule may provide for the at least one therapy parameter to be one or more of stimulus amplitude, stimulus frequency, and stimulus pulse width.

In some embodiments the neurostimulation therapy is delivered in a closed loop manner. In such embodiments the schedule may provide for the at least one therapy parameter to be one or more of:
ECAP detector parameters such as frequency and delay
Charge delivered per stimulus pulse
Stimulus frequency
ECAP target value
Feedback controller gain
Maximum stimulus intensity In some embodiments, the adjusting the at least one therapy parameter comprises determining whether the measured physiological characteristic indicates physical ageing of the patient at a rate different from an expected rate, and adjusting the at least one therapy parameter according to the schedule of adjustments if the measured physiological characteristic does not indicate physical ageing of the patient at a rate different from the expected rate.

In some embodiments, the schedule of adjustment itself may be altered based on measurements of age-related physiological characteristics. For example if the measured physiological characteristic indicates physical ageing of the patient at a rate different from an expected rate, a commensurate alteration to the schedule, for example to the ramp rate or time constant, may be made. Checks for possible such alterations to the schedule may be made on a predetermined schedule, such as periodically, and/or may be triggered by events such as a clinical reprogramming session.

References herein to estimation, determination, comparison and the like are to be understood as referring to an automated process carried out on data by a processor operating to execute a predefined procedure suitable to effect the described estimation, determination and/or comparison step(s). The technology disclosed herein may be implemented in hardware (e.g., using digital signal processors, application specific integrated circuits (ASICs) or field programmable gate arrays (FPGAs)), or in software (e.g., using instructions tangibly stored on non-transitory computer-readable media for causing a data processing system to perform the steps described herein), or in a combination of hardware and software. The disclosed technology can also be embodied as computer-readable code on a computer-readable medium. The computer-readable medium can include any data storage device that can store data which can thereafter be read by a computer system. Examples of the computer-readable medium include read-only memory ("ROM"), random-access memory ("RAM"), magnetic tape, optical data storage devices, flash storage devices, or any other suitable storage devices. The computer-readable medium can also be distributed over network-coupled computer systems so that the computer-readable code is stored and/or executed in a distributed fashion.

BRIEF DESCRIPTION OF THE DRAWINGS

One or more implementations of the invention will now be described with reference to the accompanying drawings, in which.

DETAILED DESCRIPTION OF PREFERRED EMBODIMENTS

Figure 1:
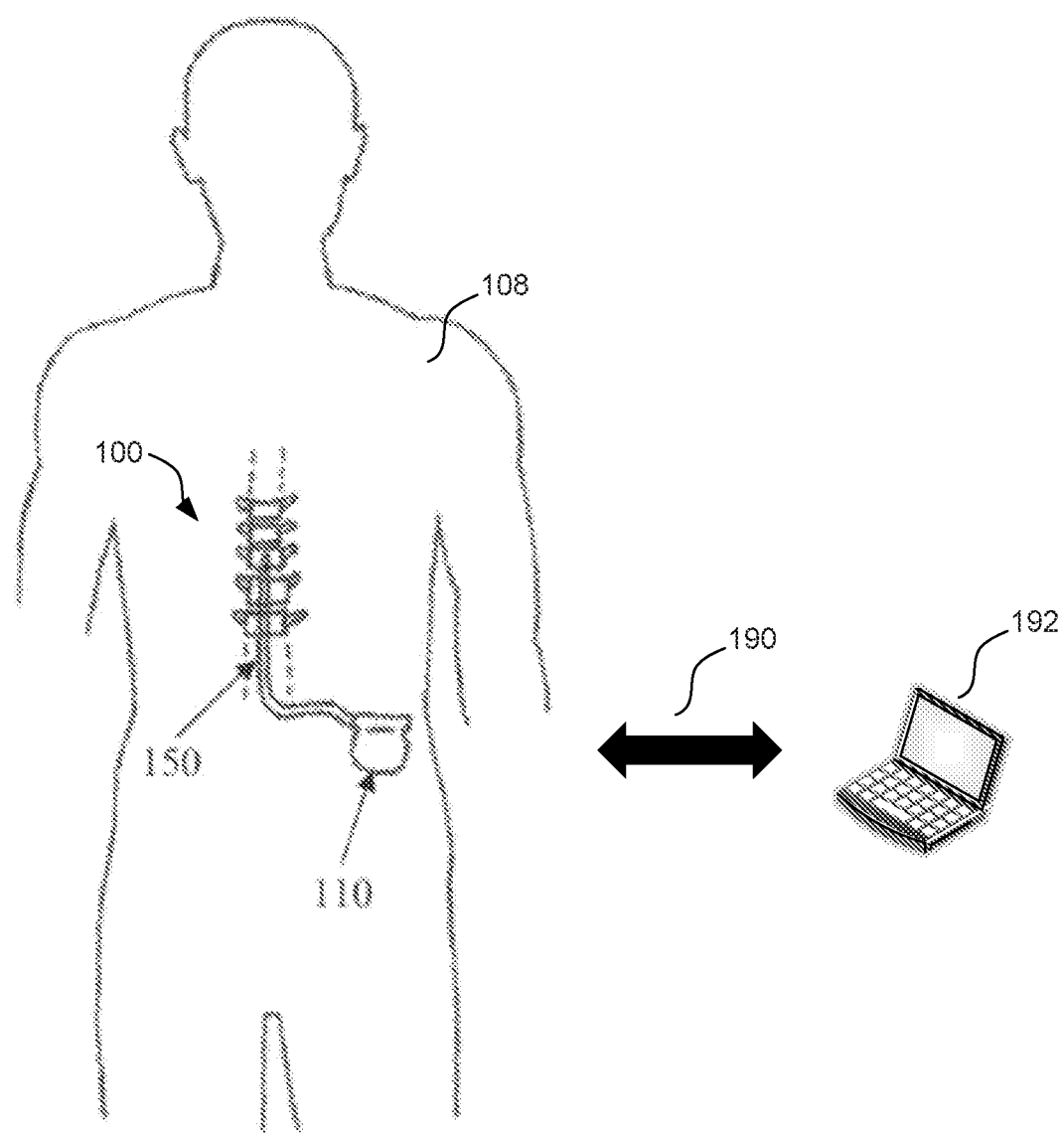
FIG. 1 schematically illustrates an implanted spinal cord stimulator, according to one implementation of the present technology.

FIG. 1 schematically illustrates an implanted spinal cord stimulator 100 in a patient 108, according to one implementation of the present technology. Stimulator 100 comprises an electronics module 110 implanted at a suitable location. In one implementation, stimulator 100 is implanted in the patient's lower abdominal area or posterior superior gluteal region. In other implementations, the electronics module 110 is implanted in other locations, such as a flank or subclavicular. Stimulator 100 further comprises an electrode array 150 implanted within the epidural space and connected to the module 110 by a suitable lead. The electrode array 150 may comprise one or more electrodes such as electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for stimulation and measurement. The electrodes may pierce or affix directly to the tissue itself.

Numerous aspects of the operation of implanted stimulator 100 may be programmable by an external computing device 192, which may be operable by a user such as a clinician or the patient 108. Moreover, implanted stimulator 100 serves a data gathering role, with gathered data being communicated to external device 192 via a transcutaneous communications channel 190. Communications channel 190 may be active on a substantially continuous basis, at periodic intervals, at non-periodic intervals, or upon request from the external device 192. External device 192 may thus provide a clinical interface configured to program the implanted stimulator 100 and recover data stored on the implanted stimulator 100. This configuration is achieved by program instructions collectively referred to as the Clinical Programming Application (CPA) and stored in an instruction memory of the clinical interface.

Figure 2:
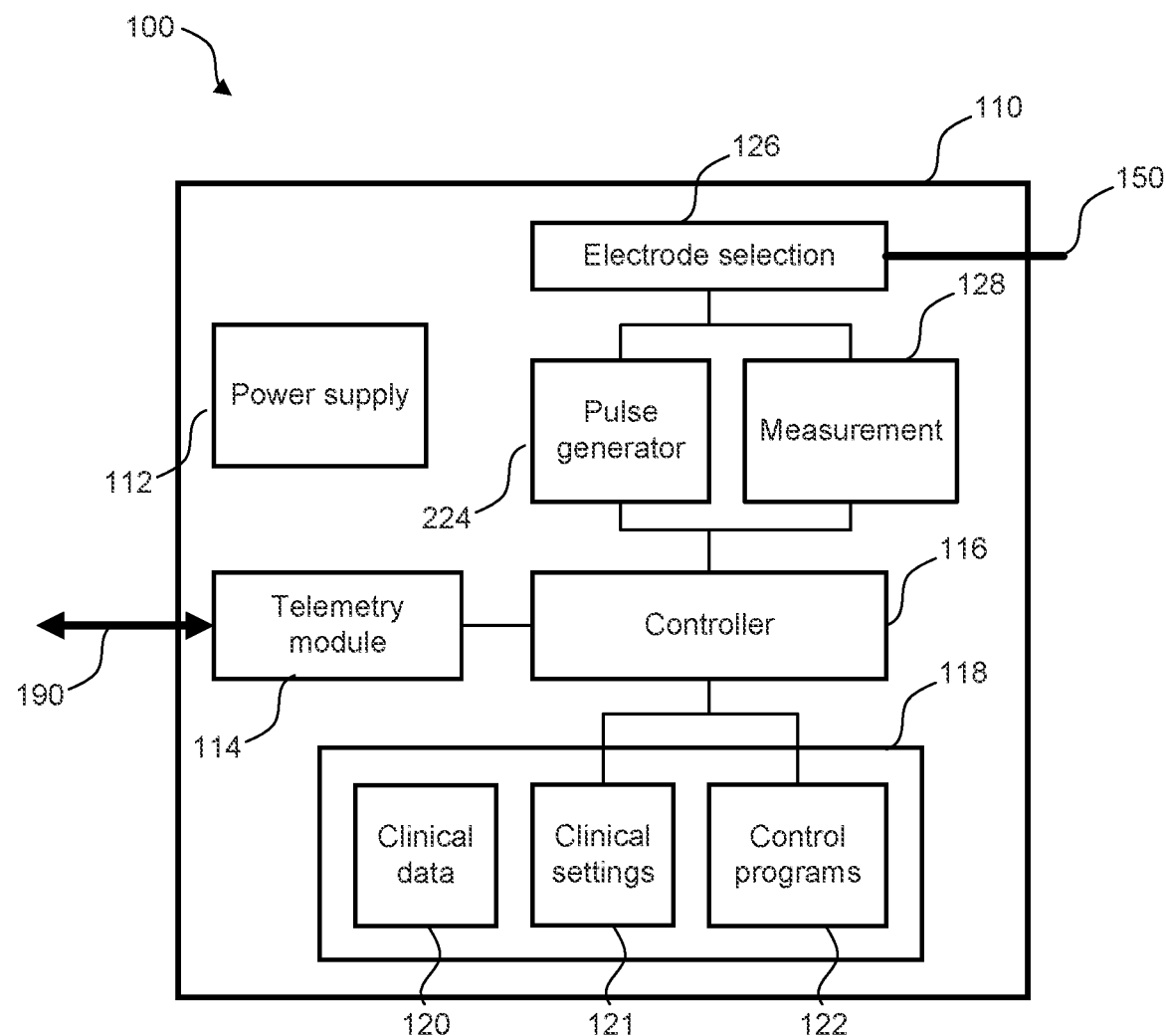
FIG. 2 is a block diagram of the stimulator of FIG. 1.

FIG. 2 is a block diagram of the stimulator 100. Electronics module 110 contains a battery 112 and a telemetry module 114. In implementations of the present technology, any suitable type of transcutaneous communication channel 190, such as infrared (IR), radiofrequency (RF), capacitive and inductive transfer, may be used by telemetry module 114 to transfer power and/or data to and from the electronics module 110 via communications channel 190. Module controller 116 has an associated memory 118 storing one or more of clinical data 120, clinical settings 121, control programs 122, and the like. Controller 116 is configured by control programs 122 to control a pulse generator 124 to generate stimuli, such as in the form of electrical pulses, in accordance with the clinical settings 121 and control programs 122. Electrode selection module 126 switches the generated pulses to the selected electrode(s) of electrode array 150, for delivery of the pulses to the tissue surrounding the selected electrode(s). Measurement circuitry 128, which may comprise an amplifier and/or an analog-to-digital converter (ADC), is configured to process signals comprising neural responses sensed at measurement electrode(s) of the electrode array 150 as selected by electrode selection module 126.

Figure 3:
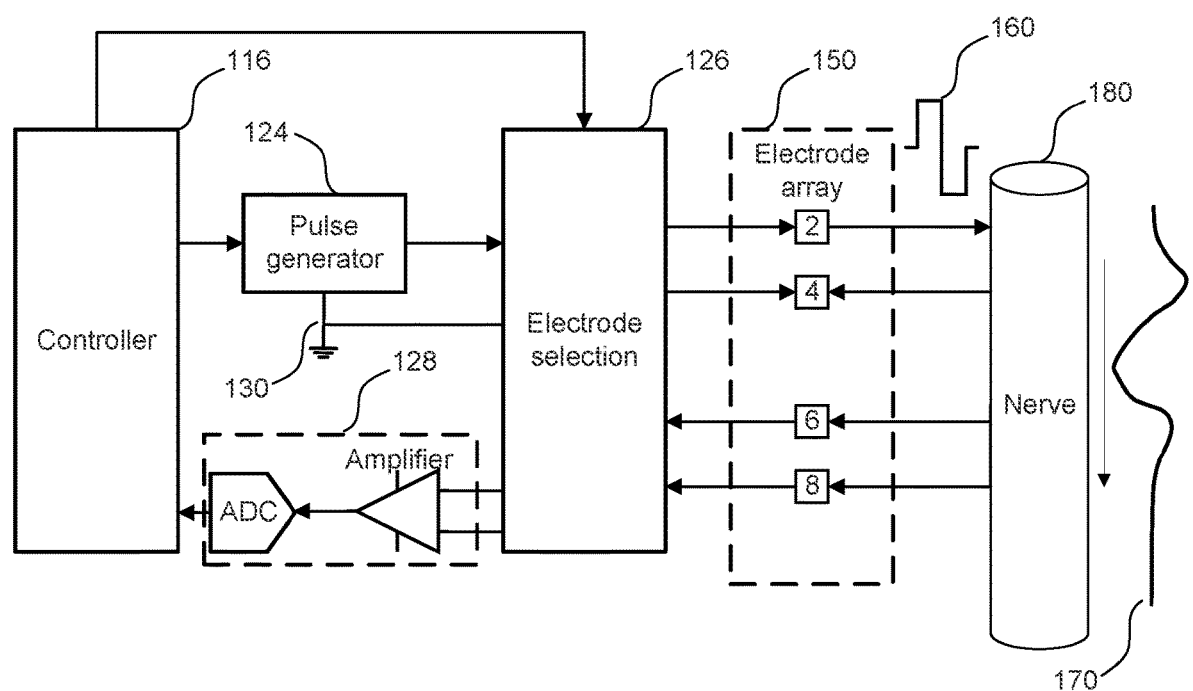
FIG. 3 is a schematic illustrating interaction of the implanted stimulator of FIG. 1 with a nerve.

FIG. 3 is a schematic illustrating interaction of the implanted stimulator 100 with a nerve 180 in the patient 108. In the implementation illustrated in FIG. 3 the nerve 180 may be located in the spinal cord, however in alternative implementations the stimulator 100 may be positioned adjacent any desired neural tissue including a peripheral nerve, visceral nerve, parasympathetic nerve or a brain structure. Electrode selection module 126 selects a stimulus electrode 2 of electrode array 150 through which to deliver a pulse from the pulse generator 124 to surrounding tissue including nerve 180. A pulse may comprise one or more phases, e.g. a biphasic stimulus pulse 160 comprises two phases. The electrode selection module 126 selects a stimulus electrode 2 to deliver the pulse to surrounding tissue including nerve 180. Electrode selection module 126 also selects a return electrode 4 of the electrode array 150 for stimulus charge recovery in each phase, to maintain a zero net charge transfer. The use of two electrodes in this manner for delivering and recovering current in each stimulus phase is referred to as bipolar stimulation. Alternative embodiments may apply other forms of bipolar stimulation, or may use a greater number of stimulus electrodes. Electrode selection module 126 is illustrated as connecting to a ground 130 of the pulse generator 124 to enable stimulus charge recovery via the return electrode 4. However, other connections for charge recovery may be used in other implementations.

Delivery of an appropriate stimulus from stimulus electrodes 2 and 4 to the nerve 180 evokes a neural response 170 comprising an evoked compound action potential 170 (ECAP) which will propagate along the nerve 180 as illustrated at a rate known as the conduction velocity. The ECAP may be evoked for therapeutic purposes, which in the case of a spinal cord stimulator for chronic pain may be to create paraesthesia at a desired location. To this end, the stimulus electrodes 2 and 4 are used to deliver stimuli periodically at any therapeutically suitable frequency, for example 30 Hz, although other frequencies may be used including frequencies as high as the kHz range. In alternative implementations, stimuli may be delivered in a non-periodic manner such as in bursts, or sporadically, as appropriate for the patient 108. To "fit" or program the stimulator 100 to the patient 108, a clinician may cause the stimulator 100 to deliver stimuli of various configurations which seek to produce a sensation that is experienced by the user as paraesthesia. When a stimulus configuration is found which evokes paraesthesia in a location and of a size which is congruent with the area of the patient's body affected by pain and of a quality that is comfortable for the patient, the clinician nominates that configuration for ongoing use. The therapy parameters may be loaded into the memory 118 of the stimulator 100 as the clinical settings 121.

Figure 6:
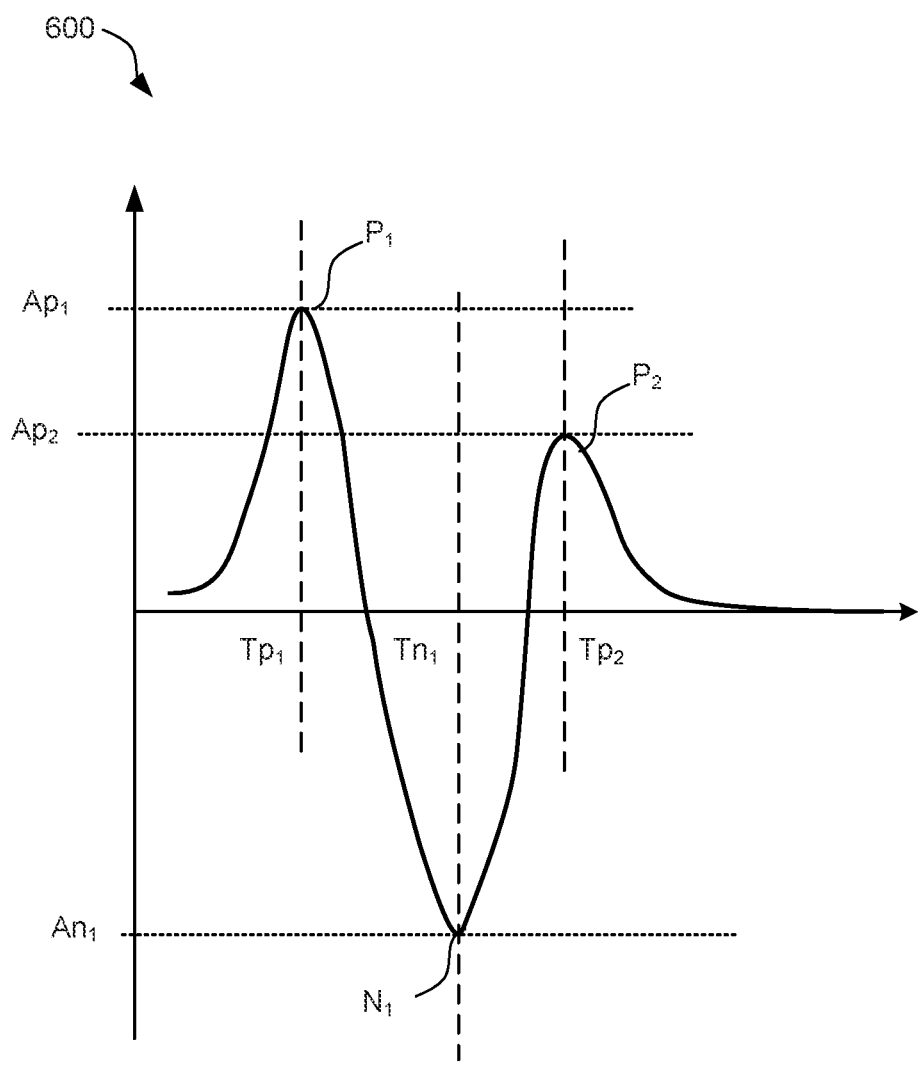
FIG. 6 illustrates the typical form of an electrically evoked compound action potential (ECAP) of a healthy subject.

FIG. 6 illustrates the typical form of an ECAP 600 of a healthy subject, as recorded at a single measurement electrode referenced to the system ground 130. The shape and duration of the single-ended ECAP 600 shown in FIG. 6 is predictable because it is a result of the ion currents produced by the ensemble of fibres depolarising and generating action potentials (APs) in response to stimulation. The evoked action potentials (EAPs) generated synchronously among a large number of fibres sum to form the ECAP 600. The ECAP 600 generated from the synchronous depolarisation of a group of similar fibres comprises a positive peak P1, then a negative peak N1, followed by a second positive peak P2. This shape is caused by the region of activation passing the measurement electrode as the action potentials propagate along the individual fibres.

The ECAP may be recorded differentially using two measurement electrodes, as illustrated in FIG. 3. Depending on the polarity of recording, a differential ECAP may take an inverse form to that shown in FIG. 6, i.e. a form having two negative peaks N1 and N2, and one positive peak P1. Alternatively, depending on the distance between the two measurement electrodes, a differential ECAP may resemble the time derivative of the ECAP 600, or more generally the difference between the ECAP 600 and a time-delayed copy thereof.

The ECAP 600 may be parametrised by any suitable parameter(s) of which some are indicated in FIG. 6. The amplitude of the positive peak P1 is $Ap_1$ and occurs at time $Tp_1$. The amplitude of the positive peak P2 is $Ap_2$ and occurs at time $Tp_2$. The amplitude of the negative peak P1 is $An_1$ and occurs at time $Tn_1$. The peak-to-peak amplitude is $Ap_1+An_1$. A recorded ECAP will typically have a maximum peak-to-peak amplitude in the range of microvolts and a duration of 2 to 3 ms.

The stimulator 100 is further configured to detect the existence and measure the intensity of ECAPs 170 propagating along nerve 180, whether such ECAPs are evoked by the stimulus from electrodes 2 and 4, or otherwise evoked. To this end, any electrodes of the array 150 may be selected by the electrode selection module 126 to serve as recording electrode 6 and measurement reference electrode 8, whereby the electrode selection module 126 selectively connects the chosen electrodes to the inputs of the measurement circuitry 128. Thus, signals sensed by the measurement electrodes 6 and 8 subsequent to the respective stimuli are passed to the measurement circuitry 128, which may comprise an amplifier and an analog-to-digital converter (ADC), as illustrated in FIG. 3. The measurement circuitry 128 for example may operate in accordance with the teachings of the above-mentioned International Patent Application Publication No. WO2012/155183.

Signals sensed by the measurement electrodes 6, 8 and processed by measurement circuitry 128 are further processed by an ECAP detector implemented within controller 116, configured by control programs 122, to obtain information regarding the effect of the applied stimulus upon the nerve 180. In some implementations, the sensed signals are processed by the ECAP detector in a manner which extracts and stores one or more parameters from each evoked neural response or group of responses contained in the sensed signal. In one such implementation, the parameter comprises a peak-to-peak ECAP amplitude in microvolts ($\mu V$). For example, the neural responses may be processed by the ECAP detector to determine the peak-to-peak ECAP amplitude in accordance with the teachings of International Patent Publication No. WO201/5074121, the contents of which are incorporated herein by reference. Alternative implementations of the ECAP detector may extract and store an alternative parameter from the neural response, or may extract and store two or more parameters from the response.

Stimulator 100 applies stimuli over a potentially long period such as days, weeks, or months and during this time may store parameters of neural responses, clinical settings, paraesthesia target level, and other operational parameters in memory 118. To effect suitable SCS therapy, stimulator 100 may deliver tens, hundreds or even thousands of stimuli per second, for many hours each day, Each neural response or group of responses generates one or more parameters such as a measure of the amplitude of the neural response. Stimulator 100 thus may produce such data at a rate of tens or hundreds of Hz, or even kHz, and over the course of hours or days this process results in large amounts of clinical data 120 which may be stored in the memory 118. Memory 118 is however necessarily of limited capacity and care is thus required to select compact data forms for storage into the memory 118, to ensure that the memory 118 is not exhausted before such time that the data is expected to be retrieved wirelessly by external device 192, which may occur only once or twice a day, or less.

Figure 4A:
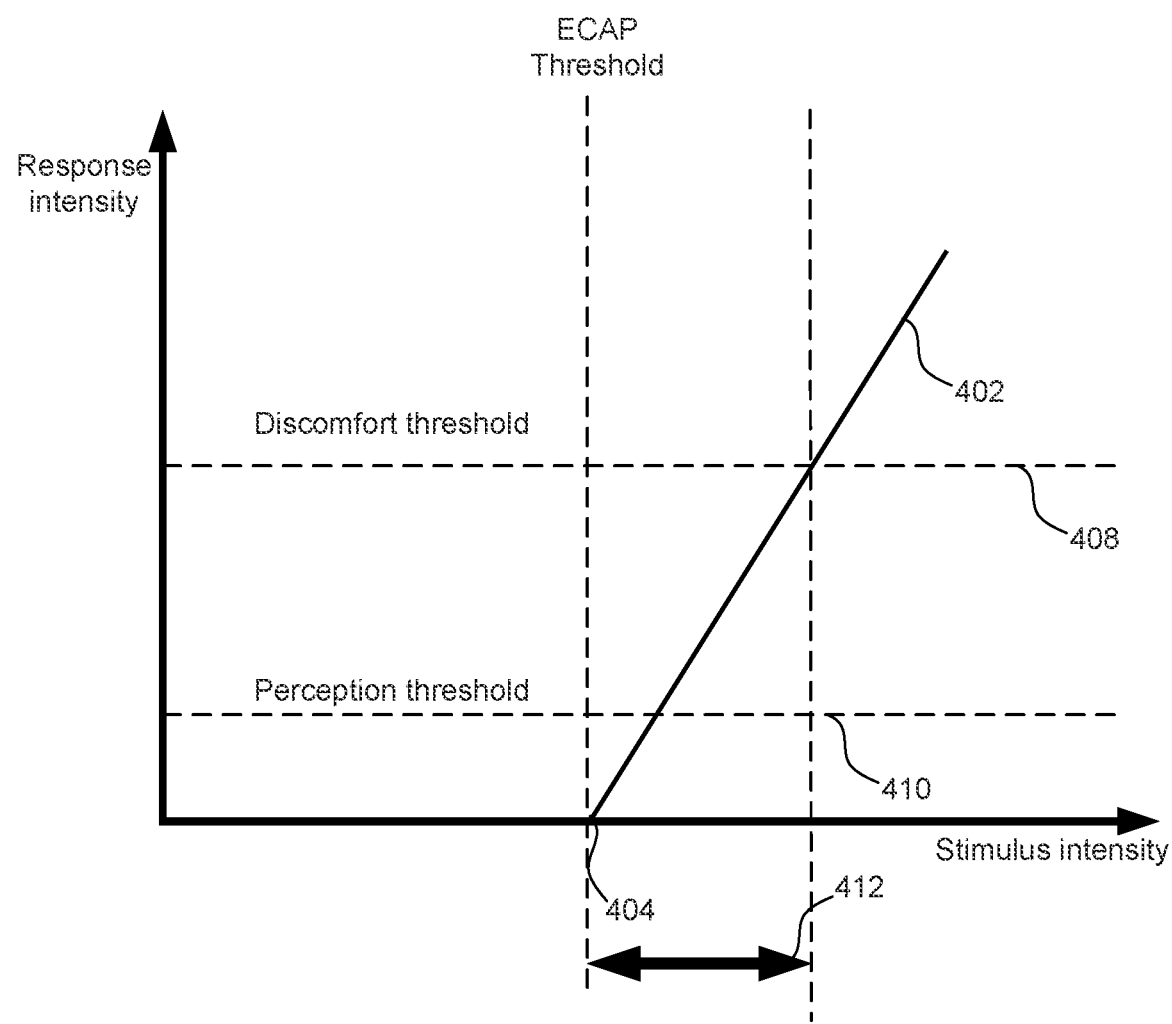
FIG. 4a illustrates an idealised activation plot for one posture of a patient undergoing neurostimulation.

An activation plot, or growth curve, is an approximation to the relationship between stimulus intensity (e.g. an amplitude of the current pulse 160) and intensity of neural response 170 evoked by the stimulus (e.g. an ECAP amplitude). FIG. 4a illustrates an idealised activation plot 402 for one posture of the patient 108. The activation plot 402 shows a linearly increasing ECAP amplitude for stimulus intensity values above a threshold 404 referred to as the ECAP threshold. The ECAP threshold exists because of the binary nature of fibre recruitment; if the field strength is too low, no fibres will be recruited. However, once the field strength exceeds a threshold, fibres begin to be recruited, and their individual evoked action potentials are independent of the strength of the field. The ECAP threshold 404 therefore reflects the field strength at which significant numbers of fibres begin to be recruited, and the increase in response intensity with stimulus intensity above the ECAP threshold reflects increasing numbers of fibres being recruited. Below the ECAP threshold 404, the ECAP amplitude may be taken to be zero. Above the ECAP threshold 404, the activation plot 402 has a positive, approximately constant slope indicating a linear relationship between stimulus intensity and the ECAP amplitude. Such a relationship may be modelled as:

$$y = \begin{cases} S(s-T), & s \geq T \\ 0, & s < T \end{cases} \quad (1)$$

where s is the stimulus intensity, y is the ECAP amplitude, T is the ECAP threshold and S is the slope of the activation plot (referred to herein as the patient sensitivity). The slope S and the ECAP threshold T are the key parameters of the activation plot 402.

FIG. 4a also illustrates a discomfort threshold 408, which is an ECAP amplitude above which the patient 108 experiences uncomfortable or painful stimulation. FIG. 4a also illustrates a perception threshold 410. The perception threshold 410 corresponds to an ECAP amplitude that is perceivable by the patient. There are a number of factors which can influence the position of the perception threshold 410, including the posture of the patient. Perception threshold 410 may correspond to a stimulus intensity that is greater than the ECAP threshold 404, as illustrated in FIG. 4a, if patient 108 does not perceive low levels of neural activation. Conversely, the perception threshold 410 may correspond to a stimulus intensity that is less than the ECAP threshold 404, if the patient has a high perception sensitivity to lower levels of neural activation than can be detected in an ECAP, or if the signal to noise ratio of the ECAP is low.

For effective and comfortable operation of an implantable neuromodulation device such as the stimulator 100, it is desirable to maintain stimulus intensity within a therapeutic range 412. A stimulus intensity within a therapeutic range 412 is above the ECAP threshold 404 and evokes an ECAP amplitude that is below the discomfort threshold 408. In principle, it would be straightforward to measure these limits and ensure that stimulus intensity, which may be closely controlled, always falls within the therapeutic range 412. However, the activation plot, and therefore the therapeutic range 412, varies with the posture of the patient 108.

Figure 4B:
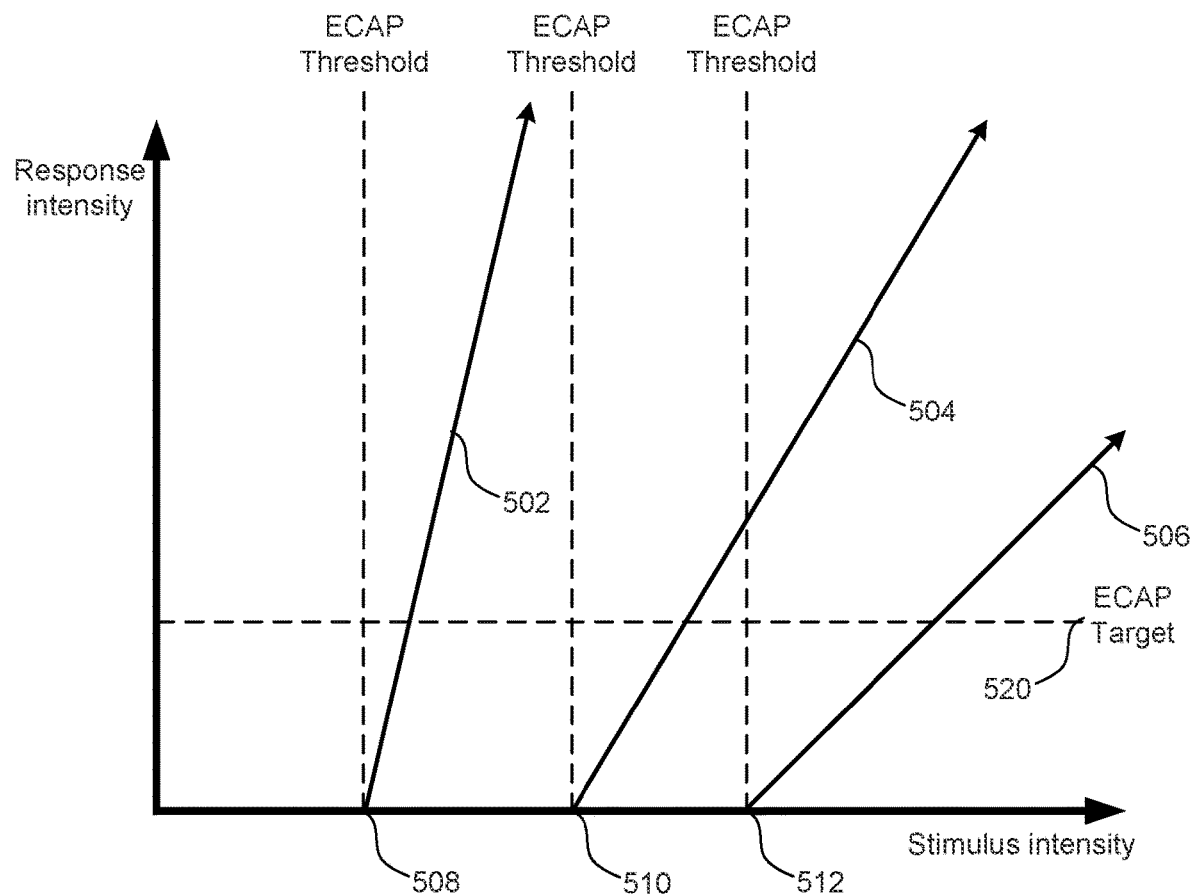
FIG. 4b illustrates the variation in the activation plots with changing posture of the patient.

FIG. 4b illustrates the variation in the activation plots with changing posture of the patient. A change in posture of the patient may cause a change in impedance of the electrode-tissue interface or a change in the distance between electrodes and the neurons. While the activation plots for only three postures, 502, 504 and 506, are shown in FIG. 4b, the activation plot for any given posture can lie between or outside the activation plots shown, on a continuously varying basis depending on posture. Consequently, as the patient's posture changes, the ECAP threshold changes, as indicated by the ECAP thresholds 508, 510, and 512 for the respective activation plots 502, 504, and 506. Additionally, as the patient's posture changes, the slope of the activation plot also changes, as indicated by the varying slopes of activation plots 502, 504, and 506. In general, as the distance between the stimulus electrodes and the spinal cord increases, the ECAP threshold increases and the slope of the activation plot decreases. The activation plots 502, 504, and 506 therefore correspond to increasing distance between stimulus electrodes and spinal cord, and decreasing patient sensitivity.

To keep the applied stimulus intensity within the therapeutic range as patient posture varies, in some implementations an implantable neuromodulation device such as the stimulator 100 may adjust the applied stimulus intensity based on a feedback variable that is determined from one or more extracted ECAP parameters. In one implementation, the device may adjust the stimulus intensity to maintain the extracted ECAP amplitude at a target response intensity. For example, the device may calculate an error between a target ECAP value and a measured ECAP amplitude, and adjust the applied stimulus intensity to reduce the error as much as possible, such as by adding the scaled error to the current stimulus intensity. A neuromodulation device that operates by adjusting the applied stimulus intensity based on an extracted ECAP parameter is said to be operating in closed-loop mode and will also be referred to as a closed-loop neural stimulation (CLNS) device. By adjusting the applied stimulus intensity to maintain the extracted ECAP amplitude at an appropriate target response intensity, such as an ECAP target 520 illustrated in FIG. 4b, a CLNS device will generally keep the stimulus intensity within the therapeutic range as patient posture varies.

A CLNS device comprises a stimulator that takes a stimulus intensity value and converts it into a neural stimulus comprising a sequence of electrical pulses according to a predefined stimulation pattern. The stimulation pattern is characterised by multiple parameters including stimulus amplitude, pulse width, number of phases, order of phases, number of stimulus electrode poles (two for bipolar, three for tripolar etc.), and stimulus rate or frequency. At least one of the stimulus parameters, for example the stimulus amplitude, is controlled by the feedback loop.

In an example CLNS system, a user (e.g. the patient or a clinician) sets a target neural response intensity, and the CLNS device performs proportional-integral-differential (PID) control. In some implementations, the differential contribution is disregarded and the CLNS device uses a first order integrating feedback loop. The stimulator produces stimulus in accordance with a stimulus intensity parameter, which evokes a neural response in the patient. The evoked neural response (e.g. an ECAP) is detected and its amplitude measured by the CLNS device and compared to the target neural response intensity.

The measured neural response amplitude, and its deviation from the target neural response intensity, is used by the feedback loop to determine possible adjustments to the stimulus intensity parameter to maintain the neural response at the target intensity. If the target intensity is properly chosen, the patient receives consistently comfortable and therapeutic stimulation through posture changes and other perturbations to the stimulus/response behaviour.

Figure 5:
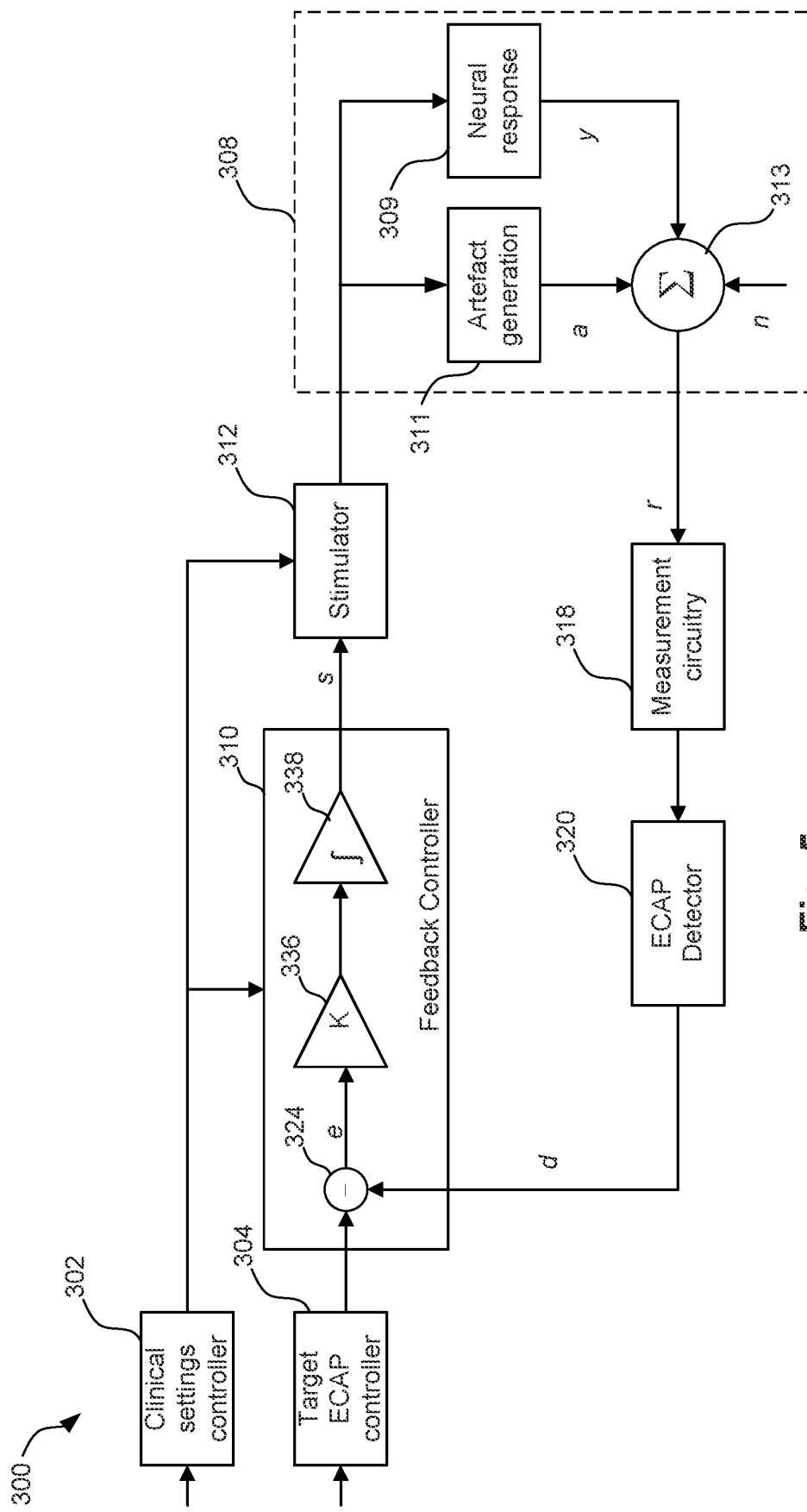
FIG. 5 is a schematic illustrating elements and inputs of a closed-loop neural stimulation system, according to one implementation of the present technology.

FIG. 5 is a schematic illustrating elements and inputs of a closed-loop neural stimulation (CLNS) system 300, according to one implementation of the present technology. The system 300 comprises a stimulator 312 which converts a stimulus intensity parameter (for example a stimulus current amplitude) s, in accordance with a set of predefined stimulus parameters, to a neural stimulus comprising a sequence of electrical pulses on the stimulus electrodes (not shown in FIG. 5). According to one implementation, the predefined stimulus parameters comprise the number and order of phases, the number of stimulus electrode poles, the pulse width, and the stimulus rate or frequency.

The generated stimulus crosses from the electrodes to the spinal cord, which is represented in FIG. 5 by the dashed box 308. The box 309 represents the evocation of a neural response y by the stimulus as described above. The box 311 represents the evocation of an artefact signal a, which is dependent on stimulus intensity and other stimulus parameters, as well as the electrical environment of the measurement electrodes. Artefact is described in more detail below. Various sources of noise n, as well as artefact a, may add to the evoked response y at the summing element 313 to form the sensed signal r, including: electrical noise from external sources such as 50 Hz mains power; electrical disturbances produced by the body such as neural responses evoked not by the device but by other causes such as peripheral sensory input; EEG; EMG; and electrical noise from measurement circuitry 318.

The neural recruitment arising from the stimulus is affected by mechanical changes, including posture changes, walking, breathing, heartbeat and so on. Mechanical changes may cause impedance changes, or changes in the location and orientation of the nerve fibres relative to the electrode array(s). As described above, the intensity of the evoked response provides a measure of the recruitment of the fibres being stimulated. In general, the more intense the stimulus, the more recruitment and the more intense the evoked response. An evoked response typically has a maximum amplitude in the range of microvolts, whereas the voltage resulting from the stimulus applied to evoke the response is typically several volts.

Measurement circuitry 318, which may be identified with measurement circuitry 128, amplifies the sensed signal r (including evoked neural response, artefact, and noise) and samples the amplified sensed signal r to capture a "signal window" comprising a predetermined number of samples of the amplified sensed signal r. The ECAP detector 320 processes the signal window and outputs a measured neural response intensity d. In one implementation, the neural response intensity comprises a peak-to-peak ECAP amplitude. The measured response intensity d is input into the feedback controller 310. The feedback controller 310 comprises a comparator 324 that compares the measured response intensity d to a target ECAP value (set by the target ECAP controller 304) and provides an indication of the difference between the measured response intensity d and the target ECAP value. This difference is the error value e. The error value e is input into the feedback controller 310.

The feedback controller 310 calculates an adjusted stimulus intensity parameter, s, with the aim of maintaining a measured response intensity d equal to the target ECAP value. Accordingly, the feedback controller 310 adjusts the stimulus intensity parameter s to minimise the error value, e. In one implementation, the controller 310 utilises a first order integrating function, using a gain element 336 and an integrator 338, in order to provide suitable adjustment to the stimulus intensity parameter s. According to such an implementation, the current stimulus intensity parameter s may be computed by the feedback controller 310 as $$s = \int Ke\,dt \quad (2)$$

where K is the gain of the gain element 336 (the controller gain).

A target ECAP value is input to the feedback controller 310 via the target ECAP controller 304. In one embodiment, the target ECAP controller 304 provides an indication of a specific target ECAP value. in another embodiment, the target ECAP controller 304 provides an indication to increase or to decrease the present target ECAP value. The target ECAP controller 304 may comprise an input into the CLNS system 300, via which the patient or clinician can input a target ECAP value, or indication thereof. The target ECAP controller 304 may comprise memory in which the target ECAP value is stored, and provided to the feedback controller 310.

A clinical settings controller 302 provides clinical settings to the system 300, including the feedback controller 310 and the stimulus parameters for the stimulator 312 that are not under the control of the feedback controller 310. In one example, the clinical settings controller 302 may be configured to adjust the controller gain K of the feedback controller 310 to adapt the feedback loop to patient sensitivity. The clinical settings controller 302 may comprise an input into the CLNS system 300, via which the patient or clinician can adjust the clinical settings. The clinical settings controller 302 may comprise memory in which the clinical settings are stored, and are provided to components of the system 300.

In some implementations, two clocks (not shown) are used, being a stimulus clock operating at the stimulus frequency (e.g. 60 Hz) and a sample clock for sampling the sensed signal r (for example, operating at a sampling frequency of 10 kHz). As the ECAP detector 320 is linear, only the stimulus clock affects the dynamics of the CLNS system 300. On the next stimulus clock cycle, the stimulator 312 outputs a stimulus in accordance with the adjusted stimulus intensity S. Accordingly, there is a delay of one stimulus clock cycle before the stimulus intensity is updated in light of the error value e.

Figure 7:
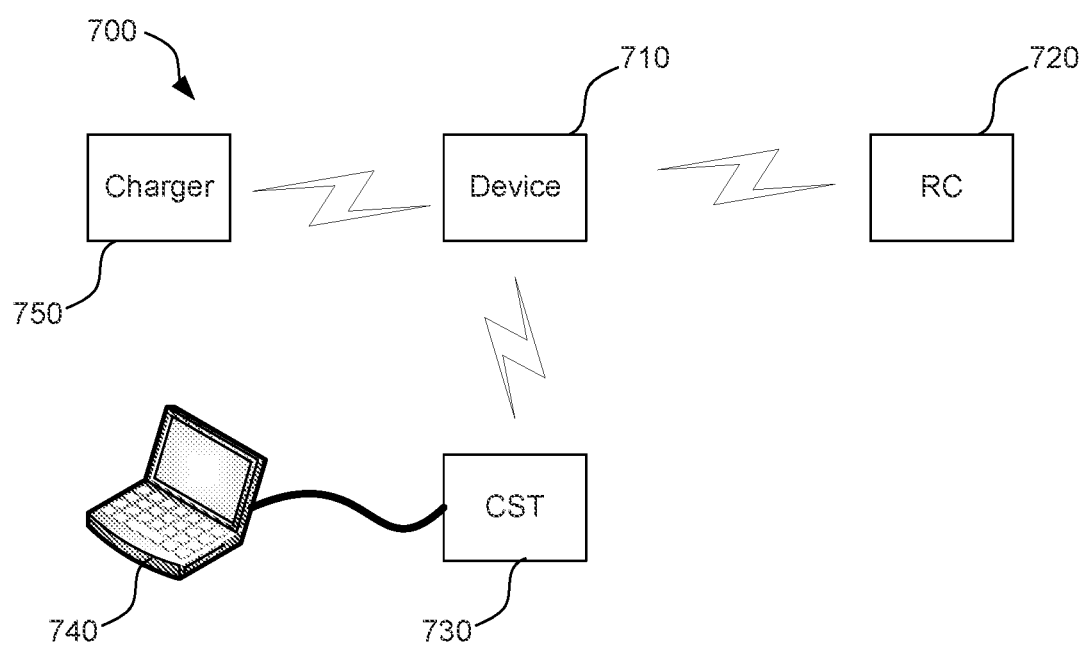
FIG. 7 is a block diagram of a neuromodulation therapy system including the implanted stimulator of FIG. 1 according to one implementation of the present technology.

FIG. 7 is a block diagram of a neuromodulation system 700. The neuromodulation system 700 is centred on a neuromodulation device 710. In one example, the neuromodulation device 710 may be implemented as the stimulator 100 of FIG. 1, implanted within a patient (not shown). The neuromodulation device 710 is connected wirelessly to a remote controller (RC) 720. The remote controller 720 is a portable computing device that provides the patient with control of their stimulation in the home environment by allowing control of the functionality of the neuromodulation device 710, including one or more of the following functions: enabling or disabling stimulation; adjustment of stimulus intensity or target neural response intensity; and selection of a stimulation control program from the control programs stored on the neuromodulation device 710.

The charger 750 is configured to recharge a rechargeable power source of the neuromodulation device 710. The recharging is illustrated as wireless in FIG. 7 but may be wired in alternative implementations.

The neuromodulation device 710 is wirelessly connected to a Clinical System Transceiver (CST) 730. The wireless connection may be implemented as the transcutaneous communications channel 190 of FIG. 1. The CST 730 acts as an intermediary between the neuromodulation device 710 and the Clinical Interface (CI) 740, to which the CST 730 is connected. A wired connection is shown in FIG. 7, but in other implementations, the connection between the CST 730 and the CI 740 is wireless.

The clinical interface 740 may be implemented as the external computing device 192 of FIG. 1. The CI 740 is configured to program the neuromodulation device 710 and recover data stored on the neuromodulation device 710. This configuration is achieved by program instructions collectively referred to as the Clinical Programming Application (CPA) and stored in an instruction memory of the clinical interface 740.

Figure 8:
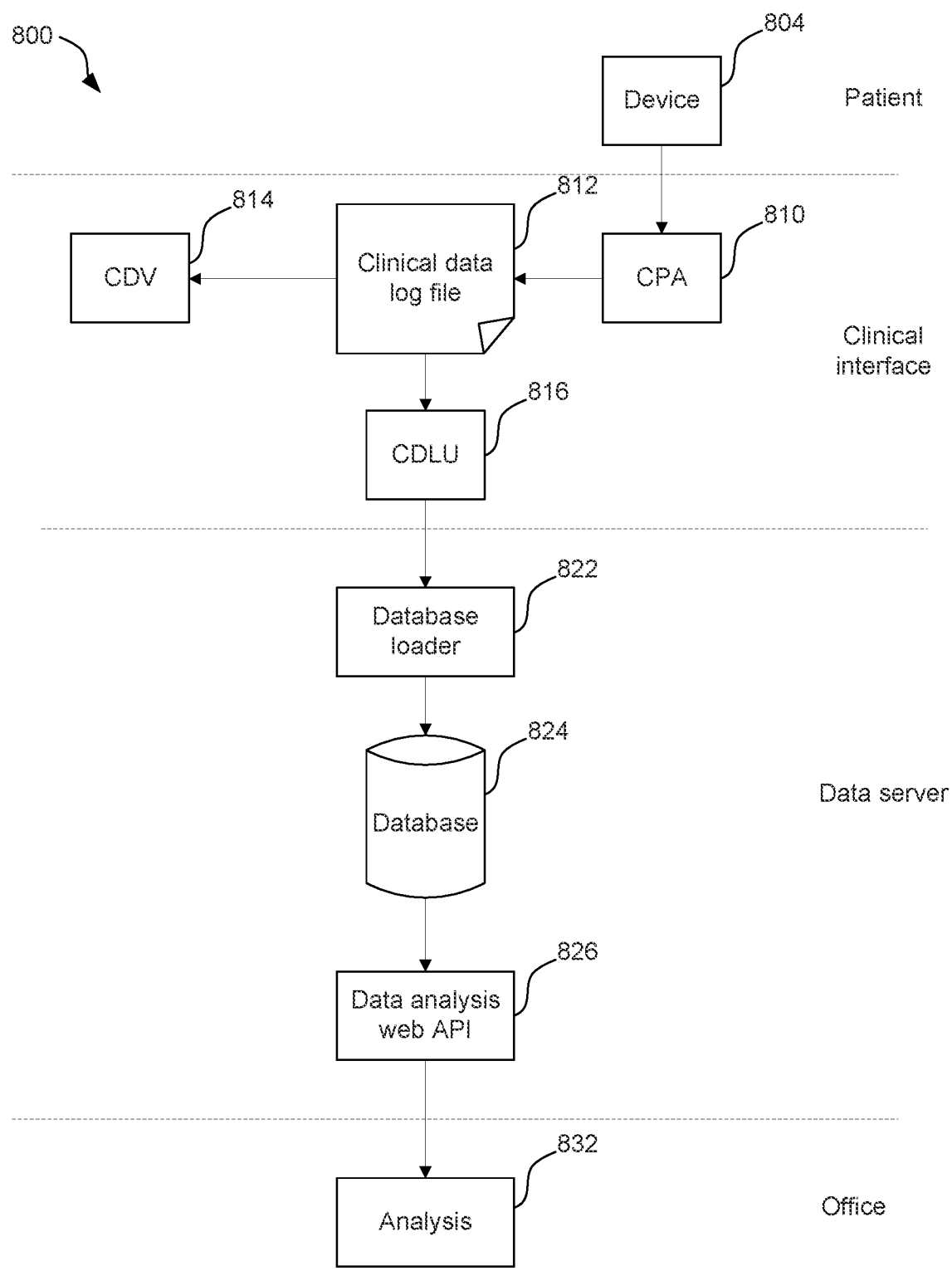
FIG. 8 is a block diagram illustrating the data flow of a neuromodulation therapy system such as the system of FIG. 7.

FIG. 8 is a block diagram illustrating the data flow 800 of a neuromodulation therapy system such as the system 700 of FIG. 7 according to one implementation of the present technology. Neuromodulation device 804, once implanted within a patient, applies stimuli over a potentially long period such as weeks or months and records neural responses, clinical settings, paraesthesia target level, and other operational parameters, discussed further below. Neuromodulation device 804 may comprise a Closed-Loop Neural Stimulation (CLNS) device, in that the recorded neural responses are used in a feedback arrangement to control clinical settings on a continuous or ongoing basis. To effect suitable SCS therapy, neuromodulation device 804 may deliver tens, hundreds or even thousands of stimuli per second, for many hours each day. The feedback loop may operate for most or all of this time, by obtaining neural response recordings following every stimulus, or at least obtaining such recordings regularly. Each recording generates a feedback variable such as a measure of the amplitude of the evoked neural response, which in turn results in the feedback loop changing at least one stimulus parameter for a following stimulus. Neuromodulation device 804 thus produces such data at a rate of tens or hundreds of Hz, or even kHz, and over the course of hours or days this process results in large amounts of clinical data. This is unlike past neuromodulation devices such as open-loop SCS devices which lack any ability to record any neural response.

When brought in range with a receiver, neuromodulation device 804 transmits data, e.g. via telemetry module 114, to a clinical programming application (CPA) 810 installed on a clinical interface. In one implementation, the clinical interface is the CI 740 of FIG. 7. The data can be grouped into two main sources: (1) Data collected in real-time during a programming session; (2) Data downloaded from a stimulator after a period of non-clinical use by a patient. CPA 810 collects and compiles the data into a clinical data log file 812.

All clinical data transmitted by the neuromodulation device 804 may be compressed by use of a suitable data compression technique before transmission by telemetry module 114 and/or before storage into the memory 118 to enable storage by neuromodulation device 804 of higher resolution data. This higher resolution allows neuromodulation device 804 to provide more data for post-analysis and more detailed data mining for events during use. Alternatively, compression enables faster transmission of standard-resolution clinical data.

The clinical data log file 812 is manipulated, analysed, and efficiently presented by a clinical data viewer (CDV) 814 for field diagnosis by a clinician, field clinical engineer (FCE) or the like. CDV 814 is a software application installed on the Clinical Interface (CI). In one implementation, CDV 814 opens one Clinical Data Log file 812 at a time. CDV 814 is intended to be used in the field to diagnose patient issues and optimise therapy for the patient. CDV 814 may be configured to provide the user or clinician with a summary of neuromodulation device usage, therapy output, and errors, in a simple single-view page immediately after log files are compiled upon device connection.

Clinical Data Uploader 816 is an application that runs in the background on the CI, that uploads files generated by the CPA 810, such as the clinical data log file 812, to a data server. Database Loader 822 is a service which runs on the data server and monitors the patient data folder for new files. When Clinical Data Log files are uploaded by Clinical Data Uploader 816, database loader 822 extracts the data from the file and loads the extracted data to Database 824.

The data server further contains a data analysis web API 826 which provides data for third-party analysis such as by the analysis module 832, located remotely from the data server. The ability to obtain, store, download and analyse large amounts of neuromodulation data means that the present technology can: improve patient outcomes in difficult conditions: enable faster, more cost effective and more accurate troubleshooting and patient status; and enable the gathering of statistics across patient populations for later analysis, with a view to diagnosing aetiologies and predicting patient outcomes.

Age Adaptation

Figure 9:
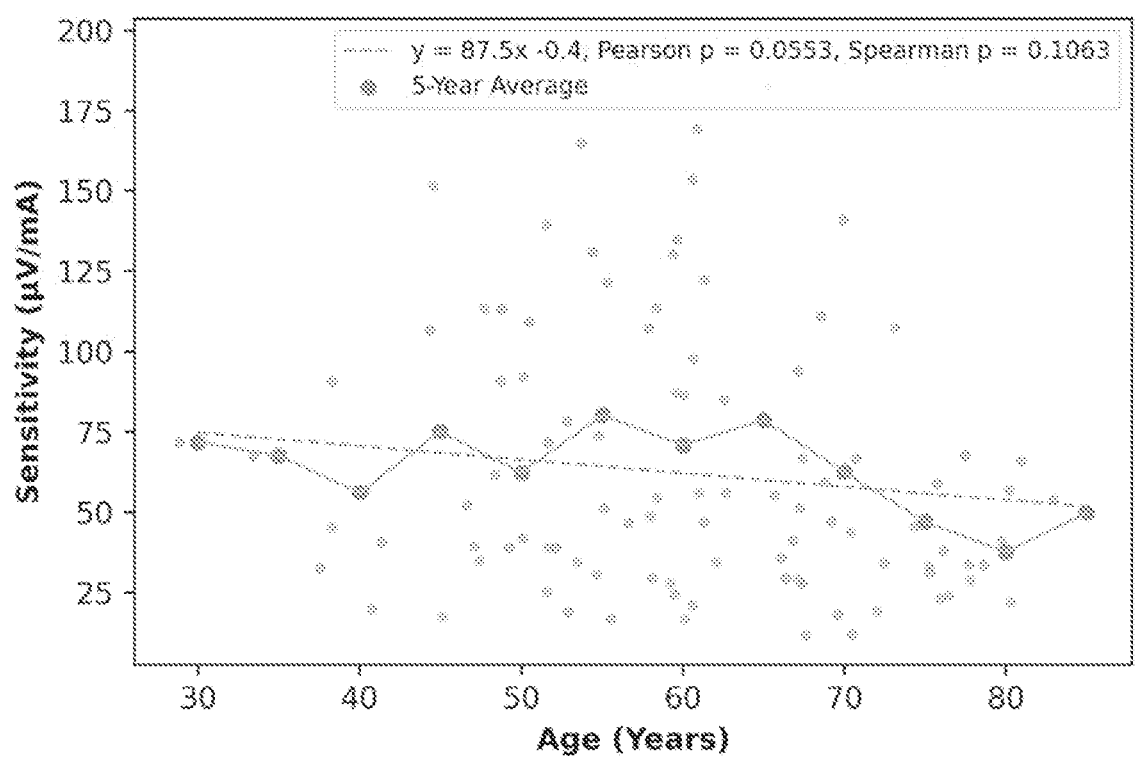
FIG. 9 contains a graph illustrating the effect of ageing on patient sensitivity.

As the human body ages, certain physiological characteristics that play a role in neurostimulation therapy, such as SCS for chronic pain management, start to change in a way that reduces the efficacy of the therapy. One example is ECAP threshold. The negative potential required to activate a fibre is related to the diameter of the fibre. As the distribution of the diameters of the population of neurons subject to stimulation changes with age, it follows that the ECAP threshold also changes over time. Another example is patient sensitivity. FIG. 9 contains a graph illustrating the decrease in patient sensitivity with patient age in years. Yet another example is ECAP conduction velocity, which like ECAP threshold is related to the changing distribution of fibre diameters. Conduction velocity affects the ECAP latency, or the time after stimulation at which the ECAP propagates past the measurement electrode(s). A related characteristic is the dispersion of the recruited fibres, which tends to increase with age, and thereby spreads and flattens the ECAP over time. Both of these characteristics affect the detectability of an ECAP by a fixed ECAP detector.

Another age-related effect is a decrease in the maximum tolerable stimulus intensity. This results in a narrowing of the therapeutic window within which comfortable, effective neurostimulation can take place.

Yet another age-related effect is the shortening of the spine with age. This will affect the ECAP latency.

Yet another effect is the reduction in posture-based variation of the activation plot (illustrated in FIG. 4B) as patients become less mobile with age and the electrode-to-cord distance varies less as a result.

The combination of these changes in physiological characteristics may have multiple effects on neurostimulation therapy:

A change in the relationship between stimulus intensity and recruitment;

A change in the relationship between stimulus intensity and comfort;

A change in the relationship between recruitment and measured ECAP parameters;

A change in the variability of loop dynamics with posture.

The first two of these effects are particularly pertinent for open-loop schemes that stimulate around the perceptual threshold. A fixed stimulus intensity will sooner or later lose its efficacy or comfort as the physiological thresholds migrate with age.

By contrast, closed-loop neural stimulation systems are inherently able to adapt to these effects to some extent by adjusting stimulus intensity to maintain the measured ECAP amplitude at the target ECAP value. However, to the extent that age-related effects affect the relationship between recruitment and the measured ECAP parameters (which may occur if the ECAP detector becomes de-tuned due to the change in ECAP shape and latency), closed-loop SCS may be unable to compensate fully for these effects. In addition, the range of stimulus intensity within which the loop can operate without discomfort is affected by age.

The result is that closed-loop neural stimulation therapy parameters which worked well at the age of implantation become less effective, and/or more uncomfortable, with advancing age. Manual reprogramming sessions to address this situation are costly and inconvenient. The present technology is therefore directed to implantable devices capable of, and methods for, self-reprogramming to adapt the therapy to age-related effects. The disclosed methods and devices are configured to adapt the therapy parameters (e.g. stimulus intensity for open-loop, or ECAP target, ECAP detector parameters, and feedback loop parameters for closed-loop) gradually over time to compensate for the age-related effects according to a predetermined schedule that may be altered in response to measurements of age-related physiological characteristics that are relevant to neurostimulation.

According to one implementation of the present technology suitable for open-loop SCS, the controller 116 of the electronics module 110 is configured to gradually and monotonically increase stimulus intensity (e.g. by increasing the amplitude, pulse width, or frequency of stimulus pulses) to compensate for the age-related effects according to a schedule. The default schedule may be predetermined, e.g. a lookup table, or a linear ramp with a certain ramp rate (i.e. a certain number of increments per unit time), or an exponential ramp with a certain time constant (i.e. a certain number of proportional increments per unit time), or some other monotonic functional form. Default schedule parameters (e.g. ramp rate or time constant) may be set per patient as part of initial programming, depending on captured patient characteristics such as starting age, gender, vital signs, and lifestyle indicators.

Adjustments to the current schedule of increase may be made based on measurements of age-related physiological characteristics. If the characteristics indicate physical ageing at a rate different from the expected rate, a commensurate alteration, for example to the ramp rate or time constant, may be made to the current schedule. Checks for such alterations to the current schedule may be made on a predetermined schedule (periodically), or triggered by events such as a reprogramming visit.

Measurements could be made invisibly to the patient by the electronics module 110, e.g. using an accelerometer forming part of the electronics module 110 to measure daily activity, a decrease in which may be indicative of advancing age. Another example of measurement requires active patient involvement, such as via an app running on a connected device such as the remote controller 720 that measures a reaction time of the patient, an increase of which may also be indicative of advancing age.

Other examples of measurement of age-related physiological characteristics using a connected device include:
  A measurement of grip strength made using a connected dynamometer.
  A measurement of maximum heart rate or heart rate variation during activity using a connected heart rate monitor.
  A measurement of forced expiratory volume or forced vital capacity using a connected spirometer.

Another implementation of the present technology is suitable for closed-loop SCS. This closed-loop implementation is based on the open-loop implementation described above. However, rather than the default schedule specifying a monotonic increase in stimulus intensity, the default schedule may specify a monotonic increase or decrease in one or more of the following closed-loop neural stimulation therapy parameters:
  ECAP detector parameters such as frequency and delay
  Charge delivered per stimulus pulse
  Stimulation frequency
  ECAP target value
  Feedback controller gain
  Maximum stimulus intensity The charge delivered per stimulus pulse may be adjusted independently of stimulus amplitude (which may be controlled by the feedback loop as described above), for example via adjusting the pulse width of each phase of a stimulus pulse, or by appending additional pulses in rapid succession to each phase of a stimulus pulse.

As with the open-loop implementation, the default schedule may be predetermined. Default schedule parameters may be set per patient during initial programming, depending on patient characteristics.

As with the open-loop implementation, alterations to the current schedule may be made based on measurements of age-related physiological characteristics. If the characteristics indicate physical ageing at a rate different from the expected rate, a commensurate alteration may be made to the current schedule. Checks for such alterations to the current schedule may be made on a predetermined schedule (periodically), or triggered by events such as a reprogramming visit.

As with the open-loop implementation, measurement could be made invisibly to the patient by the electronics module 110, or via a method requiring active patient involvement.

However, in addition to these modes of measurement common to the open-loop implementation, the ability of closed-loop systems to accurately measure neural responses such as ECAPs enables the controller 116 to directly measure age-related neurophysiological characteristics such as:
  Conduction velocity, chronaxie, or rheobase
  ECAP threshold
  Patient sensitivity
  Maximum tolerable stim intensity (e.g. from slow response)
  Non-evoked neural activity, which is a proxy for physical activity In one implementation of measurement of a physiological characteristic, conduction velocity may be measured by interleaving recording electrode changes with closed-loop control. Such interleaving may be most suitable for a period when the patient is in a known, static posture. For example, one ECAP measurement in every twenty may be used to test a different recording electrode. The ECAP measurements are ignored for the purposes of adjusting stimulus intensity, but are accumulated at each recording electrode into a single representative ECAP, for example by averaging. The controller 116 may then compute the conduction velocity from the representative ECAP at each recording electrode. Further details on how to measure conduction velocity from ECAPs at different measurement sites are given in International Patent Publication no. WO2012/155184, the contents of which are hereby incorporated by reference.

In another implementation, patient sensitivity may be estimated from the slope of the patient's activation plot, as described above.

In another implementation of measurement of a physiological characteristic, patient sensitivity may be measured by temporarily setting the controller gain to zero, i.e. converting the closed-loop system to open-loop, while the patient is in a known, static posture. The RMS noise at the output of the of the ECAP detector, i.e. the open-loop ECAP amplitude noise level, is measured. The controller gain may then be increased to a value K, and the RMS noise at the output of the of the ECAP detector, i.e. the closed-loop ECAP amplitude noise level, measured. The ratio R of the closed-loop RMS ECAP amplitude noise level to the open-loop RMS ECAP amplitude noise level is a function of the controller gain K and the patient sensitivity S. On the assumption that the noise is white (uniformly distributed with frequency), the function may be written as:

$$R = \sqrt{\frac{2}{2 - KS}}$$

Therefore, the patient sensitivity may be estimated as:

$$S = \frac{2}{K}\left(1 - \frac{1}{R^2}\right)$$

If the ECAP amplitude noise follows a distribution that is other than uniform, the patient sensitivity may be estimated from controller gain and open-loop to closed-loop noise ratio using other functions whose form depends on the noise distribution.

The controller may alter the current schedule of controller gain or ECAP target increase or decrease based on changes in patient sensitivity.

As an alternative to altering the current schedule, a therapy parameter that is not part of the current schedule, such as recording electrode location, pulse width, number of appended pulses, or pulse frequency may be adjusted to return the physiological characteristic to a baseline value upon which the current schedule is predicated, thereby obviating the need to alter the current schedule. One example is a change of recording electrode to compensate for a change in conduction velocity or spine length, which would obviate the need to change the ECAP detector delay. In another example, pulse width, number of appended pulses, or pulse frequency may be adjusted to return the sensitivity to a baseline value upon which the current schedule is predicated, thereby obviating the need to alter the current schedule.

In a further implementation suitable for a closed-loop neural stimulation system, the ECAP detector may be duplicated, with the duplicate ECAP detector enabled to adjust its parameters while the primary ECAP detector stays fixed. In one example of a parametric ECAP detector, disclosed in the above-mentioned international Patent Publication No. WO2015/074121, the parameters are delay and frequency. The parameter adjustment may be carried out by a learning algorithm, e.g. a Bayesian learning algorithm. Periodically (for example while the patient is in a known, static posture) the two ECAP detectors may be compared and, if the self-adjusting ECAP detector proves superior, its parameters may be copied to the primary ECAP detector. Adjustments to other closed-loop neurostimulation therapy parameters (e.g. loop gain and ECAP target value) may also be made in consequence once the ECAP detector is adjusted. According to this implementation, no default schedule of adjustment of closed-loop neurostimulation therapy parameters is needed.

In another implementation suitable for a closed-loop neural stimulation system, two-dimensional histograms of neural recruitment vs patient posture, as disclosed in International Patent Publication no. WO2022/040757, the contents of which are incorporated herein by reference, may be used to measure patient activity levels, via changes of posture during waking hours. Postural variation occurring due to age-related physiological changes over time can be tracked using the 2D histograms and parameter adjustment schedules can be altered accordingly.

Figure 10:
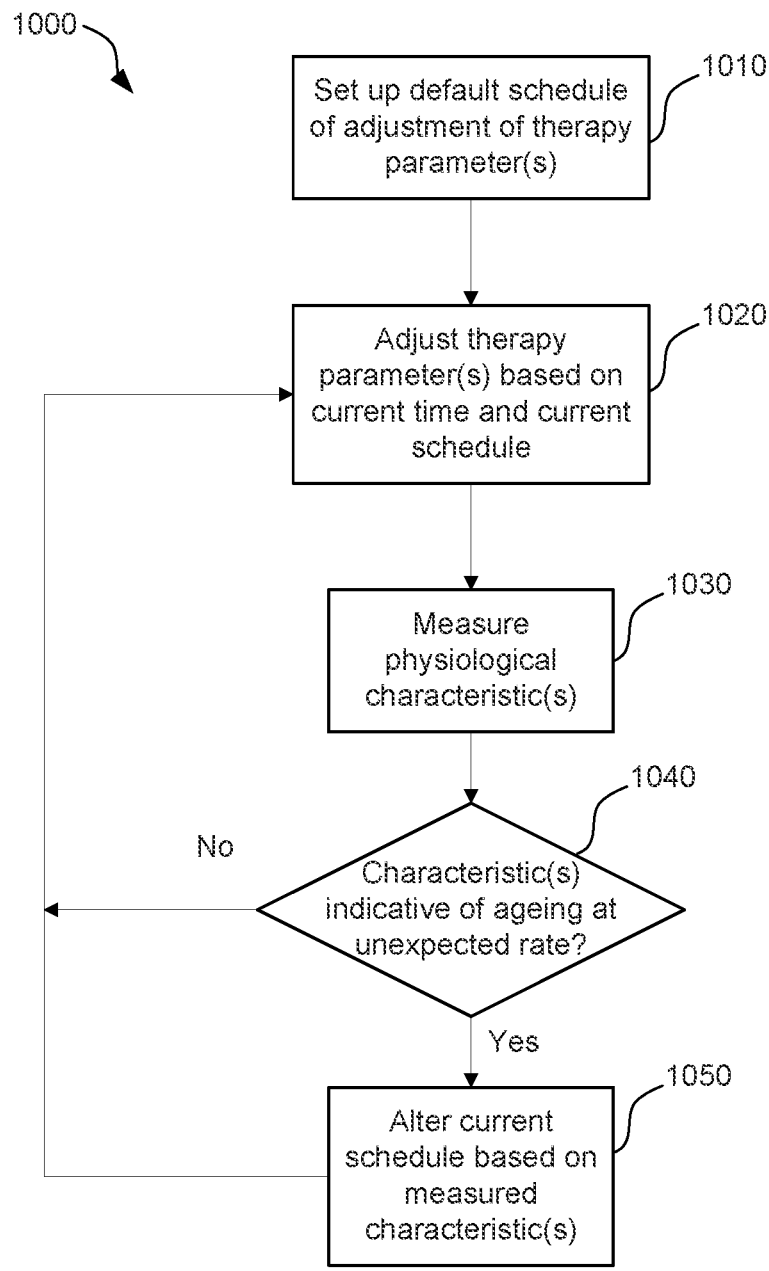
FIG. 10 is a flowchart illustrating a method of adapting SCS therapy to age-related effects on physiological characteristics of a patient, according to one implementation of the present technology.

FIG. 10 is a flowchart illustrating a method 1000 of adapting SCS therapy to age-related effects on physiological characteristics of a patient, according to one implementation of the present technology. The method 1000 may be carried out by the controller 116 of the electronics module 110 of an implantable stimulator 100, appropriately configured by executable instructions stored in the memory 118 as a control program 122. The method 1000 is suitable for an open-loop or a closed-loop implementation of SCS therapy.

The method 1000 starts at step 1010, which sets up a default schedule of adjustment of one or more therapy parameters. As described above, the adjusted parameters may be different depending on whether the therapy is open-loop or closed-loop. Step 1010 may take place during initial programming of the stimulator for a patient.

Step 1020 follows, at which therapy has commenced with the current schedule set to the default schedule. Step 1020 adjusts the therapy parameter(s) according to the current schedule and the current time since the start of therapy. The next step 1030 measures one or more age-related physiological characteristics relevant to SCS. As described above, the measured physiological characteristics may be different depending on whether the therapy is open-loop or closed-loop. Step 1030 may occur periodically, or triggered by a specified event. Step 1040 then checks whether the one or more measured physiological characteristics indicate physical ageing at a rate different from that expected by the current schedule. If so ("Yes"), step 1050 alters the current schedule according to one or more measured physiological characteristics. The method 1000 then returns to step 1020 to continue therapy according to the (altered) current schedule. If not ("No"), the method simply returns to step 1020 to continue therapy according to the current schedule.

If step 1050 alters the current schedule due to a measurement of a posture-dependent characteristics, such as patient sensitivity, step 1050 may first check that such an alteration is acceptable for all postures before the change is confirmed. For example, if a change in patient sensitivity in a certain posture indicates an alteration to the current schedule of patient controller gain adjustment is warranted, step 1050 may make the alteration provisionally, and only confirm the change once the alteration has been checked in all to ensure the therapy remains effective in each.

In a variation of the method 1000, step 1050, instead of altering the current schedule, adjusts a therapy parameter that is not part of the current schedule based on the measured physiological characteristic.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

The invention claimed is:

1. A method of adapting the operation of an implantable device for delivering neurostimulation therapy to a patient, the method comprising:
   delivering the neurostimulation therapy to electrically excitable tissue of the patient according to at least one therapy parameter;
   measuring a physiological characteristic of the patient;
   adjusting the at least one therapy parameter according to a schedule of adjustment and the measured physiological characteristic; and
   repeating the delivering, measuring, and adjusting;
   wherein the adjusting the at least one therapy parameter comprises determining whether the measured physiological characteristic indicates physical ageing of the patient at a rate different from an expected rate, and adjusting the at least one therapy parameter according to the schedule of adjustments if the measured physiological characteristic does not indicate physical ageing of the patient at a rate different from the expected rate.

2. The method of claim 1 wherein the schedule of adjustment is a predefined schedule stored in the device.

3. The method of claim 1 wherein the schedule of adjustment is altered based on the measured physiological characteristic.

4. The method of claim 3 wherein, if the measured physiological characteristic indicates physical ageing of the patient at a rate different from an expected rate, a commensurate alteration to the schedule is made.

5. The method of claim 4 wherein checks for possible alterations to the schedule are made on a predetermined schedule.

6. The method of claim 4 wherein checks for possible alterations to the schedule are triggered by a clinical reprogramming session.

7. The method of claim 1 wherein the measured physiological characteristic comprises one or more of: the patient's ECAP threshold measured in a reference posture; the patient's sensitivity to the neurostimulation therapy in a reference posture; the patient's ECAP conduction velocity; the patient's ECAP dispersion; the patient's maximum tolerable stimulus intensity in a reference posture; the patient's therapeutic window in a reference posture; the patient's ECAP latency; the patient's activation plot variation with posture; the patient's daily activity; a reaction time of the patient; a measurement of grip strength of the patient; a measurement of maximum heart rate of the patient during activity; and a measurement of forced expiratory volume of the patient.

8. The method of claim 1 wherein the neurostimulation therapy is delivered in a dosed loop manner, in which measurements are obtained of the electrical excitation effected by the neurostimulation, and the measurements are used in a feedback loop to control subsequent neurostimulation.

9. The method of claim 8 wherein the schedule provides for the at least one therapy parameter to be one or more of: ECAP detector parameters; charge delivered per stimulus pulse; Stimulus frequency; ECAP target value; Feedback controller gain; and maximum stimulus intensity.

10. The method of claim 1 wherein the neurostimulation therapy is delivered in an open loop manner.

11. The method of claim 10 wherein the schedule of adjustment provides for the at least one therapy parameter to be adjusted in a gradual manner corresponding to patient aging.

12. An implantable device for delivering neurostimulation therapy to a patient, the device comprising:
   an electrode array comprising a plurality of electrodes;
   a pulse generator connectable to the electrode array, the pulse generator configured to generate a stimulus pulse via the stimulus electrodes to electrically excitable tissue of the patient; and
   a controller configured to:
      control the pulse generator to generate the stimulus pulse according to at least one therapy parameter;
      measure a physiological characteristic of the patient;
      adjust the at least one therapy parameter according to a schedule of adjustment and the measured physiological characteristic; and
      repeat the generate, measure, and adjust;
   wherein the controller is further configured to adjust the at least one therapy parameter by determining whether the measured physiological characteristic indicates physical ageing of the patient at a rate different from an expected rate, and adjusting the at least one therapy parameter according to the schedule of adjustments if the measured physiological characteristic does not indicate physical ageing of the patient at a rate different from the expected rate.

13. The implantable device of claim 12 wherein the schedule of adjustment is a predefined schedule stored in the device.

14. The implantable device of claim 12 wherein the controller is further configured to alter the schedule of adjustment based on the measured physiological characteristic.

15. The implantable device of claim 14 wherein the controller is further configured to determine if the measured physiological characteristic indicates physical ageing of the patient at a rate different from an expected rate, and if so to make a commensurate alteration to the schedule.

16. The implantable device of claim 15 wherein the controller is further configured to make checks for possible alterations to the schedule on a predetermined schedule.

17. The implantable device of claim 12 wherein the measured physiological characteristic comprises one or more of: the patient's ECAP threshold measured in a reference posture; the patient's sensitivity to the neurostimulation therapy in a reference posture; the patient's ECAP conduction velocity; the patient's ECAP dispersion; the patient's maximum tolerable stimulus intensity in a reference posture; the patient's therapeutic window in a reference posture; the patient's ECAP latency; the patient's activation plot variation with posture; the patient's daily activity; a reaction time of the patient; a measurement of grip strength of the patient; a measurement of maximum heart rate of the patient during activity; and a measurement of forced expiratory volume of the patient.

18. The implantable device of claim 12, wherein the controller is further configured to deliver neurostimulation therapy in a closed loop manner, by obtaining measurements of the electrical excitation effected by the neurostimulation, and using the measurements in a feedback loop to control subsequent neurostimulation.

19. The implantable device of claim 18 wherein the schedule provides for the at least one therapy parameter to be one or more of: ECAP detector parameters; charge delivered per stimulus pulse; Stimulus frequency; ECAP target value; Feedback controller gain; and maximum stimulus intensity.

20. The implantable device of claim 12 wherein the controller is further configured to deliver the neurostimulation therapy in an open loop manner.

21. The implantable device of claim 20 wherein the schedule of adjustment provides for the at least one therapy parameter to be adjusted in a gradual manner corresponding to patient aging.

\* \* \* \* \*